(12) United States Patent
van Gemen et al.

(10) Patent No.: US 6,465,639 B1
(45) Date of Patent: Oct. 15, 2002

(54) METHOD FOR THE ISOLATION OF NUCLEIC ACID

(75) Inventors: Bob van Gemen, Almere (NL); Michel Mathijs Klerks, Hertogenbosch (NL); Harmannus Bernardus van Schijndel, Breda (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/600,655

(22) PCT Filed: Jan. 26, 1999

(86) PCT No.: PCT/EP99/00482

§ 371 (c)(1),
(2), (4) Date: Jul. 20, 2000

(87) PCT Pub. No.: WO99/39000

PCT Pub. Date: Aug. 5, 1999

(30) Foreign Application Priority Data

Jan. 30, 1998 (EP) .............................. 98200273

(51) Int. Cl.⁷ ........................ C07H 21/00; C07H 22/02; C07H 21/04; C07H 1/06
(52) U.S. Cl. ................... 536/25.4; 536/25.41; 536/127
(58) Field of Search ............................. 536/25.4, 25.41, 536/127

(56) References Cited

U.S. PATENT DOCUMENTS 5,075,430 A * 12/1991 Little

FOREIGN PATENT DOCUMENTS

| EP | 0 389 063 A2 | 3/1990 |
| EP | 0 747 388 A1 | 7/1990 |
| WO | WO 95/04140 * | 2/1995 |

OTHER PUBLICATIONS

Boom et al., "Rapid and Simple Method for Purification of Nucleic Acids," Journal of Clinical Microbiology, 1990, vol. 28, No. 3, pp. 495–503.
F.M. Ausuble, "Current Protocols in Molecular Biology," Wiley & Sons, 1993.

* cited by examiner

*Primary Examiner*—Samuel Barts
*Assistant Examiner*—Michael C. Henry
(74) *Attorney, Agent, or Firm*—Myers Bigel Sibley & Sajovec

(57) ABSTRACT

The present invention relates to a method for isolating nucleic acid from a sample. Known methods for the isolation of nucleic acid from these materials may comprise the use of a chaotropic substance, for example to lyse cells present in the starting material, and free the nucleic acid therefrom. When a nucleic acid containing material is treated with a chaotrope and contacted with a nucleic acid binding solid phase, the nucleic acid will bind to the solid phase in the presence of the chaotrope and the solid phase with the nucleic acid bound thereto can thus be separated from the remainder of the sample. The method of the present invention for the isolation of nucleic acid from nucleic acid containing starting material is a method wherein the starting material is contacted with a chaotropic substance and, either simultaneously or subsequently, with a nucleic acid binding solid phase, where after the nucleic acid binding solid phase is subjected to a washing procedure and, optionally, the nucleic acid is eluted from the nucleic acid binding solid phase, characterized in that the washing procedure comprises the steps of washing the solid phase with subsequently ode ore more high salt buffer solution(s), optionally an alcoholic solution and a low salt buffer solution.

21 Claims, 4 Drawing Sheets

METHOD FOR THE ISOLATION OF NUCLEIC ACID

This is the national phase application of PCT/E99/00482, filed Jan. 26, 1999.

FIELD OF THE INVENTION

The present invention relates to a method for isolating nucleic acid from a sample.

BACKGROUND OF THE INVENTION

Recent developments in molecular biology such as, nucleic acid amplification methods, recombinant DNA techniques and sequencing methods rely on isolated nucleic acids as input material. Thus there is an ongoing need to improve the methods presently used for the purification of nucleic acid from complex samples. Of course these methods should be as simple and fast as possible and should result in a high recovery of the nucleic acid from the starting material. Furthermore it would be desirable to have methods that can be readily automated. Starting materials from which DNA is to be isolated are usually complex biological materials in which the nucleic acid is present surrounded by cellular material such as proteins or lipids. Such materials may be, for example, whole blood, blood serum, buffy coat, urine, faeces, liquor cerebrospinalis, sperm, saliva, cell cultures etc.

Known methods for the isolation of nucleic acid from these materials may comprise the use of a chaotropic substance, for example to lyse cells present in the starting material, and free the nucleic acid therefrom. By chaotropic substance is meant any substance capable of altering the secondary, tertiary and/or quaternary structure of proteins and nucleic acids, but leaving at least the primary structure intact. Examples of chaotropic substances are guanidinium (iso) thiocyanate and guanidine hydrochloride. Also sodium iodine, potassium iodine, sodium (iso)thiocyanate, urea or mutual combinations therewith are suitable.

When a nucleic acid containing material is treated with a chaotrope and contacted with a nucleic acid binding solid phase, the nucleic acid will bind to the solid phase in the presence of the chaotrope and the solid phase with the nucleic acid bound thereto can thus be separated from the remainder of the sample. Solid phases used in these processes usually comprise siliceous material such as glass particles, either porous or non-porous, silica gel, glass fiber, filters made of siliceous material, diatomeceous earth, etc. Such a method, based on the use of a chaotropic substance and a nucleic acid binding solid phase is described in EP389063, the contents of which are herewith incorporated by reference. In this patent a method for the isolation of nucleic acid is described based on the use of a chaotropic substance and silica or a derivative thereof. The method can be used for the isolation of nucleic acid from complex biological starting material. With the method as described in EP 389063 nucleic acid is bound to silica in the presence of a chaotrope. Thereafter the solid phase with the nucleic acid bound thereto is separated from the liquid and washed.

In practice, washing is usually performed in a sequence of washing steps, The solid phase is usually washed with a high salt buffer, that resembles the binding buffer in its constitution. One or more wash step with a lower alkyl alcohol, such as ethanol 70% are part of the washing procedure, to remove proteins, lipids and the like that may also have been bound to the silica. The washing procedure may also involve an additional wash step with acetone to remove any remaining impurities from the silica. The volatile acetone is removed again by drying the solid phase prior to the elution of the nucleic acid therefrom with a low salt buffer.

Prior art procedures have the disadvantage that they are still rather time consuming due to these complicated washing procedures involved. Especially the use of organic solvents like acetone also makes it more difficult to automate the process. The volatile nature of the solvents used puts severe constraints on a possible apparatus to be designed for performing these methods in an automated manner.

Thus a need exists for methods that are less complicated as far as the washing procedure is concerned and thus easier to perform in an automated manner. The present invention provides such a method. The present invention resembles prior art methods in that it is based on the binding of nucleic acid to a solid phase in the presence of a chaotropic substance. However, with the method of the present invention the washing procedure has been simplified and the need for washing with acetone or drying the solid phase prior to elution is eliminated.

SUMMARY OF THE INVENTION

The method of the present invention for the isolation of nucleic acid from nucleic acid containing starting material is a method wherein the starting material is contacted with a chaotropic substance and, either simultaneously or subsequently, with a nucleic acid binding solid phase, where after the nucleic acid binding solid phase is subjected to a washing procedure and, optionally, the nucleic acid is eluted from the nucleic acid binding solid phase, characterized in that the washing procedure comprises the steps of washing the solid phase with subsequently one or more high salt buffer solution(s)
optionally an alcoholic solution
a low salt buffer solution.

DETAILED DESCRIPTION OF THE INVENTION

In nucleic acid isolation methods guanidine(iso) thiocyanate is often used in lysis buffers.

However, in cases where the nucleic acid to be isolated is intended to be used as input material for amplification reactions the guanidine ions may disturb the amplification reaction if they are not washed away properly. The high salt buffer used in the washing procedure of the method of the present invention preferably is NaSCN. By washing with NaSCN the guanidine ions that were present in the lysis buffer are replaced by natrium (sodium) ions of the high salt wash buffer.

With the method of the invention(one on the high salt buffer(s) used may comprise 1–10 M NaSCN/10 mM tris. The pH of such buffers may vary from 6 to 8 with an optimum around 6.5. Good results were obtained with a buffer having a NaSCN concentration of 10 2–5M/10 mM tris and a pH of 6.5.

Another high salt buffer that may be used in the washing procedure that is part of the method of the present invention may comprise NaCl preferably in a concentration between 1–10M. A preferred NaCl buffer comprises 2–5M NaCl/10 mM tris and has a pH of about 6.5.

To facilitate the transfer from chaotropic high salt buffer to the low salt buffer used in the washing procedure, it is advantageous to wash the solid phase with the nucleic acid bound thereto first with a NaSCN containing buffer (which will result in the replacement of guanidine ions by natrium ions) and subsequently with a NaCl buffer (resulting in the replacement of thiocyanate with chloride ions).

Thus the washing procedure may comprise the subsequent steps of, washing with a first high salt buffer comprising 1–10M NaSCN/10 mM tris, with a pH approximately between 6 and 8 and washing with a second high salt buffer comprising 1–10M NaCl/10 mM tris, with a pH approximately between 6 and 8, with a preference for a concentration of 2–5M of NaSCN and NaCl respectively and a pH of 6.5 for both buffers.

The wash steps with the high salt buffers may be followed by washing with a lower alkyl alcohol, for example, ethanol or isopropanol, to decrease the concentration of the salts (i.e. NaSCN and NaCl) from the solid phase in the sample. Furthermore, the alcohol wash steps decrease the concentration of lipids in the sample. In the case ethanol is used the preferred concentration range is about 60–70% ethanol. A most preferred concentration of ethanol is 63%. In the case of isopropanol an concentration of about 50% is preferred. The method may comprise more than one wash step with the alcoholic solution. Good results were obtained with a method comprising two subsequent washes with 70% ethanol.

The washing procedure of the method according to the present invention involves washing with a low salt buffer solution after washing with (one or more) high salt buffer(s) and optionally with a lower alkyl alcohol. With the use of the low salt buffer ethanol is removed from the solid phase. The use of the low salt buffer eliminates the need for an acetone wash and subsequent drying prior to elution of the nucleic acid from the solid phase. Elution normally is carried out with a low salt buffer or water. It is therefore surprising that the washing of the solid phase with a low salt buffer solution as performed with the method according to the invention, does not result in elution of a substantial part of the nucleic acid from the solid phase.

A preferred low salt buffer used with the method of the invention comprises 2–30 mM NaCl/10 mM tris. Good results were obtained with a low salt buffer comprising 15 mM NaCl/10 mM tris and having a pH of 6–8.

After washing with the low salt buffer, the nucleic acid may directly be eluted from the solid phase. It has been found that the addition of a weak chaotrope, for example betaine, to the elution buffer has an advantageous effect on the elution. When betaine is used in the elution buffer, the concentration may be around 3 M. Stronger chaotropes may be used in the elution buffer as well, be it in lower concentrations. Any chaotropic agent that is used to enhance the elution of the nucleic acid from the solid phase must be added at concentration that does not disturb any downstream use of the nucleic acid, for instance in nucleic acid amplification methods or direct hybridization methods.

EXAMPLES

Preface

The following examples demonstrate the mechanism and utility of the present invention. They are not limiting and should not be considered as such. Standard isolations were performed according to protocol Y described in EP389063 and by Boom et al. (1990, *J. Clin. Microbiol.* 28: 495–503), and is further referred to as the Boom protocol.

Analysis of the isolated nucleic acids was performed by several methods described in the examples. In case where the analysis is performed with the NASBA nucleic acid amplification method the following ingredients and conditions were used: 40 mM tris, pH 8.5, 70 mM KCl, 12 mM $MgCl_2$, 5 mM DTT, 1 mM each dNTP, 2 mM rATP, 2 mM rCTP, 2 mM rUTP, 1.5 mM rGTP, 0.5 mM ITP, 0.2 $\mu$M each oligonucleotide, 375 mM sorbitol, 0.105 g/l BSA, 6.4 units AMV-RT, 32 units T7 RNA polymerase, 0.08 units *E. coli* RNase H and a specified amount of template (i.e. isolated nucleic acid) in 20 $\mu$l volume. The protocol that was used consisted of mixing the isolated nucleic acid with the ingredients described above except for the enzymes, heating to 65° C. for 5 minutes, cooling to 41° C., addition of enzymes and incubation at 41° for 90 minutes.

Amplifications with NASBA were done with control RNA's (internal standards, named Qa, Qb and Qc, respectively), with known concentrations, which were added before the amplification. Also a sample (called a 100% sample) was amplified with the same internal standards, without being subjected to nucleic acid isolation. This must represent the theoretical signal for a recovery in the isolation of 100%. The detection of the amplification products was done by electrochemiluminescense according to previously described protocols (B. van Gemen et al., 1994, A one-tube quantitative HIV-1 RNA NASBA nucleic acid amplification assay using electrochemiluminescent (ECL) labeled probes. *J. Virol. Methods.* 49: 157–168).

Radioactive labeled RNA ($^{32}$P labeled RNA) was made by standard in vitro transcription protocols with incorporation of $^{32}$P-ATP in the RNA. The different fractions of the isolation method used (see examples) were analyzed for the presence of $^{32}$P-RNA in a liquid scintillation counter.

Example 1

Figure 1:
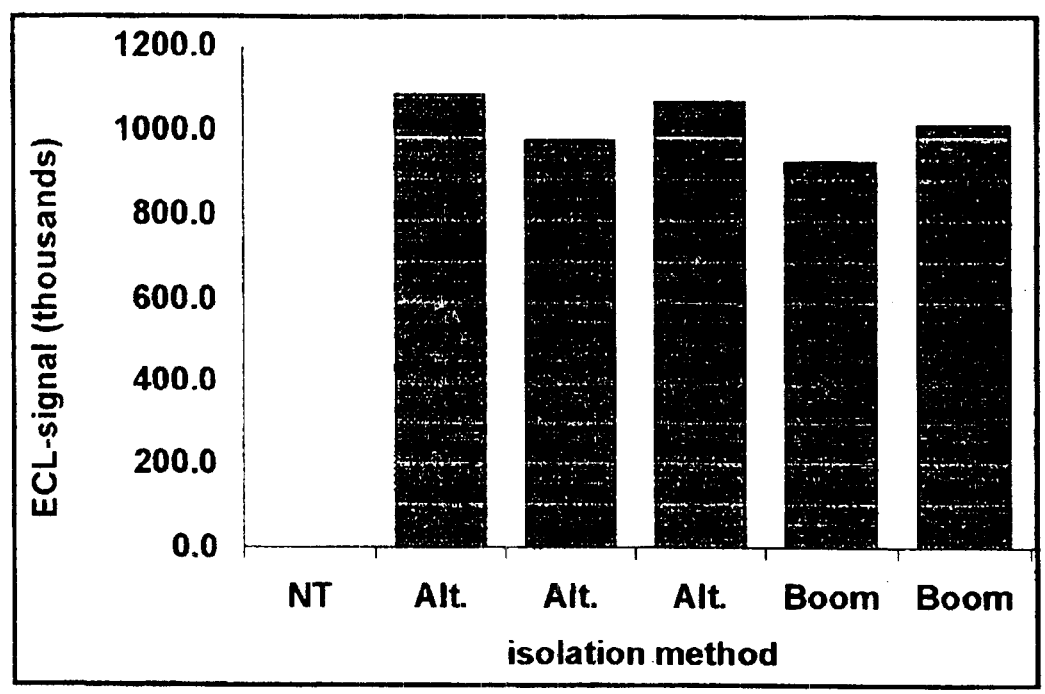
FIG. 1: The ECL signals after nucleic acid isolation by the alternative method (alt.) and the Boom method, followed by NASBA amplification and ECL detection. In vitro transcribed HIV-RNA was spiked in plasma.

In the standard Boom isolation, the nucleic acids are eluted from the solid phase in water or 1 mM tris. An alternative, new protocol was used, with surprising results (FIG.
1). The alternative protocol consisted of the following steps:
Binding of the nucleic acid to silica in the Boom lysis buffer.
Washing two times with high salt solution (5M NaSCN)
Washing two times with low salt solution (15 mM NaCl) elution with H$_2$O In a preliminary experiment (FIG. 1) this alternative protocol seemed to result in yields that are comparable with the standard Boom isolation protocol. In subsequent examples the protocol is worked out in more detail.

Example 2

Figure 2:
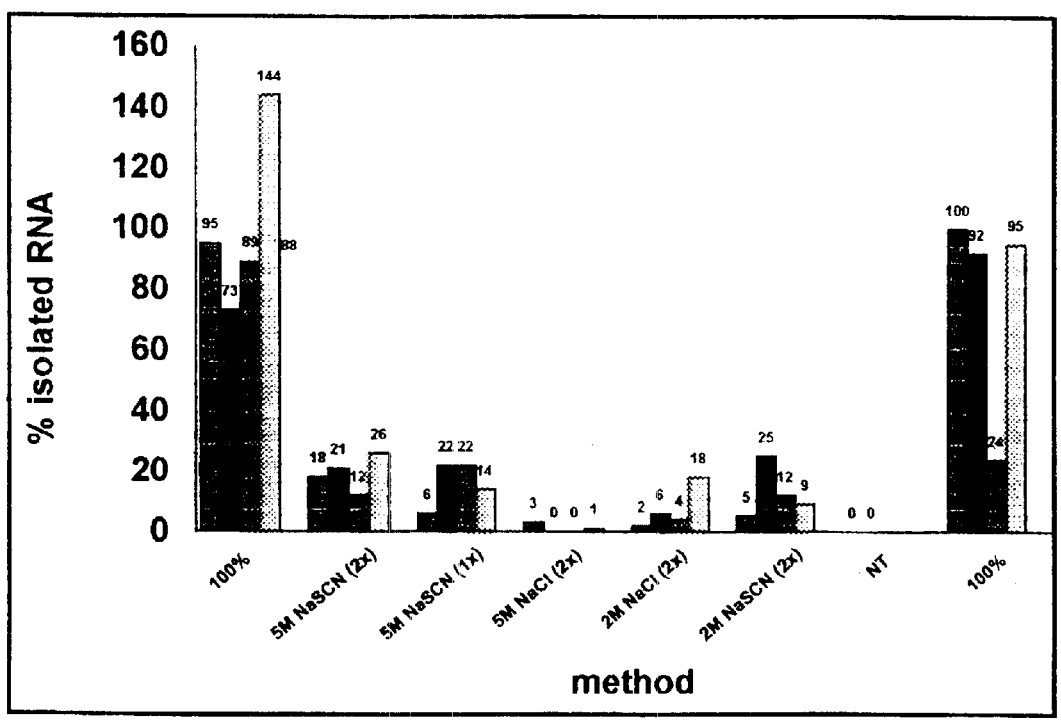
FIG. 2: In the alternative isolation method different high salt solutions were analyzed. In vitro transcribed HIV-1 RNA was spiked in plasma and the different buffers in the wash steps were tested. Summarized are the RNA recoveries after quantitative amplification and ECL detection. The samples were tested in quadruplicate.

Different solutions with high salt concentrations are analyzed in the aforementioned alternative protocol in the first washing steps. Isolations were performed with 10$^5$ molecules in vitro transcribed HIV-1 RNA spiked in plasma. After washing with the different salt solutions (see FIG. 2) and elution with H$_2$O, amplification with internal standard RNA's (2×10$^4$ Qa and 5×10$^3$ Qb) was performed. The quantitative detection of amplicons was done by ECL, the results are depicted in FIG. 2.

Washing with 2 and 5 M NaSCN is both possible, with the wash steps with 5 M NaSCN being a little better in terms of yield compared to the 2 M NaSCN wash steps. Also NaSCN seems to give more yield than NaCl in these high salt wash steps.

Example 3

To determine the optimal pH of the washing and elution buffer in the alternative isolation procedure, isolations with different pH of the low salt buffer and the elution buffer were performed. The washing buffers were 15 mM NaCl in 10 mM tris with different pH and the elution buffers were 10 mM tris with different pH.

Figure 3:
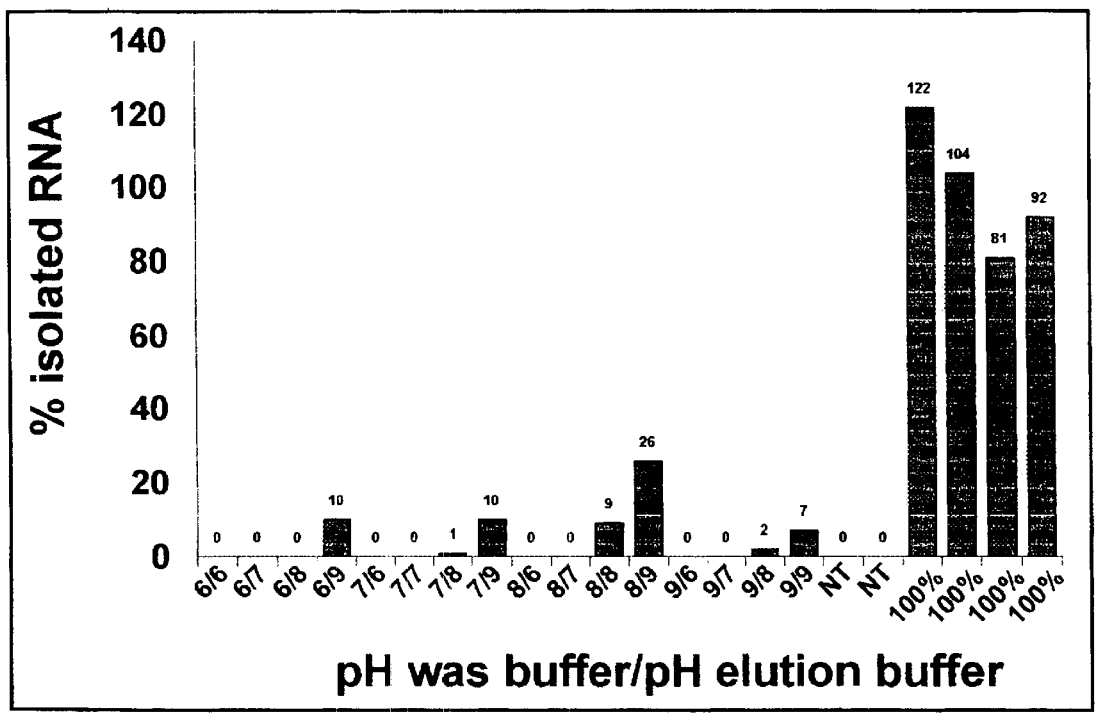
FIG. 3: Analyses of the wash buffer at different pH and the elution buffer at different pH. RNA recoveries after quantitative amplification and detection by ECL.

To 3.6 ml lysis buffer 0.4 ml plasma, 3.2×10$^6$ molecules in vitro transcribed HIV-1 RNA and 800 µl silica were added. The silica was washed two times with 5 M NaSCN/ 10 mM tris, pH 7. The silica was aliquoted into 4 tubes and each tube was washed twice with a different pH wash buffer. Again the silica from each tube was aliquoted into 4 equal parts and incubated with elution buffer with different pH. From the results depicted in FIG. 3 it seemed that washing with 15 mM NaCl/10 mM tris at pH 6, 7 or 8 gave comparable results. The elution buffer can best have pH 8 or 9.

Example 4

To check the efficiency of the different steps in the alternative isolation protocol RNA was labeled with $^{32}$P ATP and spiked in plasma. By labeling the RNA it can be followed perfectly throughout the procedure and can be measured in all the different steps of the isolation.

Purified, $^{32}$P labeled in vitro transcribed HIV-1 RNA was spiked in plasma. Isolation was performed according to the alternative procedure described above with 5M NaSCN (2×), 15 mM NaCl/10 mM tris, pH 7 (2×) and elution with 10 mM tris, pH 8.5. From each step 50 µl was added to 3 ml scintillation fluid and counted in the scintillator.

From the results (table 1) it became clear that not all the labeled material was bound to the silica. Also in the first 15 mM NaCl/10 mM tris wash step much material was lost. Further, it appeared that not all the labeled material was eluted from the silica.

In comparable experiments with the Boom isolation it was also observed that not all the material was eluted from the silica.

TABLE 1

Analyses of the wash steps in the alternative isolation. Percentage RNA in each wash step for six different samples.

| Wash step of the isolation | Sample | | | | | |
|---|---|---|---|---|---|---|
| | 1 | 2 | 3 | 4 | 5 | 6 |
| Lysis | 56% | 60% | 51% | 52% | 48% | 45% |
| 5M NaSCN | 1% | 1% | 1% | 1% | 1% | 1% |
| 5M NaSCN | 0% | 0% | 0% | 0% | 0% | 0% |
| 15 mM NaCl/10 mM Tris | 28% | 24% | 33% | 29% | 33% | 36% |
| 15 mM NaCl/10 mM Tris | 0% | 0% | 2% | 1% | 3% | 4% |
| 10 mM tris pH = 8.5 | 5% | 5% | 5% | 5% | 5% | 5% |
| silica | 10% | 10% | 9% | 11% | 10% | 10% |

Example 5

In the following example next to the introduction of the 70% ethanol wash step a comparison was made between washing with 5M NaSCN and 5M NaCl. All samples were tested in duplicate. Again, purified, $^{32}$P labeled in vitro transcribed HIV-1 RNA was spiked in plasma and used as input for the isolation. In the isolation, washing was done with either 5M NaSCN or 5M NaCl followed by two times washing with 70% ethanol and two times with 15 mM NaCl/10 mM tris, pH 6.5. Elution was done with 10 mM tris, pH 8.5.

TABLE 2

Analyses of the wash steps in the new isolation procedure. Percentage RNA in each wash step for two different samples in two different methods. A) for washing with 5 M NaSCN and B) for washing with 5 M NaCl.

| Wash buffer | Sample | | | |
|---|---|---|---|---|
| | A1 | A2 | B1 | B2 |
| Lysis-buffer | 48% | 60% | 39% | 38% |
| 5 M NaSCN | 0% | 0% | | |
| 5 M NaCl | | | 2% | 2% |
| Ethanol 70% | 0% | 0% | 0% | 0% |
| Ethanol 70% | 0% | 0% | 0% | 0% |
| 15 mM NaCl/10 mM Tris | 4% | 5% | 2% | 0% |
| 15 mM NaCl/10 mM Tris | 0% | 0% | 0% | 0% |

TABLE 2-continued

Analyses of the wash steps in the new isolation procedure. Percentage RNA in each wash step for two different samples in two different methods. A) for washing with 5 M NaSCN and B) for washing with 5 M NaCl.

| Wash buffer | Sample | | | |
|---|---|---|---|---|
| | A1 | A2 | B1 | B2 |
| 10 mM Tris | 4% | 2% | 9% | 12% |
| Silica-pellet | 44% | 25% | 36% | 37% |

Analysis of the results (table 2) revealed a slight loss of material in the wash step with 5M NaCl and no loss of material with 5M NaSCN and with 70% ethanol. In the first wash with 15 mM NaCl/10 mM tris pH 6.5 about 4% of the material was lost in all cases. A better elution was obtained by washing with 5M NaCl and less material was lost in the 15 mM NaCl/10 mM tris, pH 6.5.

Example 6

In the standard isolation procedure according to "Boom" elution of the nucleic acid from the silica is done with either $H_2O$ or 1 mM tris, pH=8.5. Elution with different concentrations of NaCl were tested in $H_2O$, 1 mM tris (pH=8.5). and 10 mM tris, pH 8.5. For each buffer 18 samples were isolated with $2 \times 10^5$ molecules in vitro transcribed HIV-1 RNA and two no template samples from plasma. Elution with different NaCl concentrations were tested in triplicate. After the isolation the samples were quantified by NASBA amplification with internal standard RNA's ($10^4$ Qa and $10^3$ Qb).

TABLE 3

The percentage nucleic acid recovery after standard Boom isolation with different amounts of salt in the elution buffer. Elution was performed with different NaCl concentrations in water, 1 mM Tris (pH = 8.5) and 10 mM Tris (pH = 8.5). The conditions were tested in triplicate.

| Concentration NaCl in the elution buffer | Water | | | 1 mM TRIS pH 8.5 | | | 10 mM TRIS pH 8.5 | | |
|---|---|---|---|---|---|---|---|---|---|
| | 1 | 2 | 3 | 1 | 2 | 3 | 1 | 2 | 3 |
| 0 mM NaCl | 78% | 150% | 69% | 9% | 16% | 9% | 11% | 30% | 17% |
| 2 mM NaCl | 1% | 2% | 2% | 0% | 15% | 22% | 15% | 22% | 12% |
| 4 mM NaCl | 1% | 0% | 1% | 0% | 0% | 4% | 56% | 11% | 16% |
| 6 mM NaCl | 0% | 0% | 0% | 0% | 0% | 16% | 40% | 49% | 18% |
| 8 mM NaCl | 1% | 1% | 0% | 0% | 3% | 0% | 54% | 35% | 66% |
| 10 mM NaCl | 1% | 0% | 2% | 0% | 0% | 1% | 0% | 43% | 79% |

The results are summarized in table 3. The presence of NaCl in the elution with water interferes very strong with the elution of the RNA, no RNA was detected after amplification. In the elution with 1 mM tris only 4 mM NaCl is tolerated. In contrast, the effect of NaCl (up to 10 mM) in 10 mM tris with pH 8.5 seems to be minimal.

Example 7

To make a statistical assessment concerning the "quality" of the isolation a comparison of the efficiency of the new isolation protocol vs. the Boom protocol was made using 20 samples. For each sample $2 \times 10^5$ copies in vitro transcribed HIV-1 RNA were spiked in plasma. Elution was performed in 100 µl $H_2O$ in the standard Boom protocol. After binding of the RNA to the silica, the new protocol existed of washings with 5M NaSCN, 5M NaCl, 70% ethanol (2×), 15 mM NaCl/10 mM tris pH=6.5 (2×) and elution in 10 mM tris, pH 8.5. After the isolation a quantitative NASBA amplification was performed by adding $10^4$ Qa and $10^5$ Qb RNA molecules as internal standards.

TABLE 4

The statistical figures of the isolation of 20 samples with the Boom method and the protocol Z.
(avg = average; std = standard deviation; cv = variation coefficient)

| Definition/method | BOOM | New protocol |
|---|---|---|
| avg | 42,4 | 18,1 |
| std | 18,5 | 8,9 |
| cv | 44% | 49% |

From these results the yield of the isolation according Boom appeared to be better (avg. 42%) compared to the protocol Z yield (avg. 18%).

Example 8

The new protocol could become much better with a more efficient elution. For the investigation of improved elution in the new protocol purified, $^{32}P$ labeled in vitro transcribed HIV-1 RNA was spiked in plasma. Isolation was performed according the above outlined new protocol (but with only one 15 mM NaCl/10 mM tris washing) and different solutions were tested in the elution step. Analyzed were 10 mM tris elution (pH=9) with the addition of 10 or 100 mM NaSCN or 100 or 3000 mM N,N,N trimethylglycine (betaine). Also the effect of an extra washing step with 15 mM NaCl/10 mM tris, pH 6.5 just prior to elution was investigated.

The elution was improved (table 5) by addition of 100 mM NaSCN or 3 M betaïne to the elution buffer.

TABLE 5

Analyses of different elution buffers in the alternative isolation. Depicted in the table is the percentage RNA measured in each fraction.

| Wash buffer | Sample 1 | 2 | 3 | 4 | 5 | 6 |
|---|---|---|---|---|---|---|
| Lysis buffer | 4% | 6% | 7% | 4% | 5% | 4% |
| 5M NaSCN | 1% | 1% | 1% | 1% | 1% | 1% |
| 5M NaCl | 0% | 0% | 0% | 0% | 0% | 0% |
| Ethanol 70% | 0% | 0% | 0% | 0% | 0% | 0% |
| Ethanol 70% | 0% | 0% | 0% | 0% | 0% | 0% |
| 15 mM NaCl/10 mM Tris | 4% | 4% | 8% | 6% | 12% | 9% |
| 15 mM NaCl/10 mM Tris | 0% | | | | | |
| 10 mM Tris | 4% | | | | | |
| 10 mM NaSCN/10 mM Tris | | 0% | | | | |
| 100 mM NaSCN/10 mM Tris | | | 57% | | | |
| 100 mM betaine/10 mM Tris | | | | 1% | | |
| 3M betaine/10 mM Tris | | | | | 62% | |
| Elution buffer | | | | | | 6% |
| Silica-pellet | 86% | 88% | 25% | 87% | 19% | 79% |

Example 9

To analyze the relative improvement of the new protocol by the addition of betaine to the elution buffer, isolation experiments were performed according to the new protocol, with or without betaïne in the elution buffer. As a control also three samples were isolated according to the standard Boom protocol. For each sample $2 \times 10^5$ molecules in vitro transcribed HIV-1 RNA were spiked in plasma. The Boom protocol was performed with elution in 100 μl H2O. After binding of the RNA to the silica, the new protocol existed of washings with 5M NaSCN, 5M NaCl, 70% ethanol (2×), 15 mM NaCl/10 mM tris, pH 6.5 and elution with 3M betaïne in 10 mM tris, pH 8.5. After the isolation a quantitative amplification was performed by adding $10^4$ Qa and $5 \times 10^3$ Qb RNA molecules as internal standards.

Figure 4:
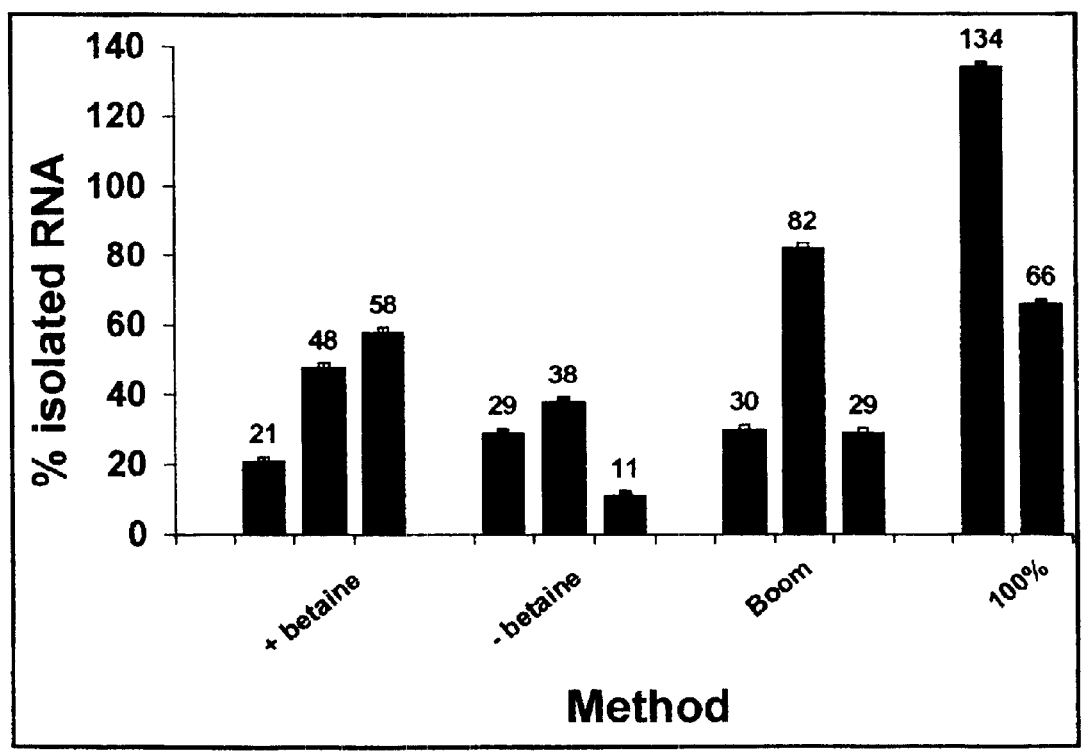
FIG. 4: Percentage RNA isolated with the new protocol with and without betaine, compared to the standard protocol Boom. The percentage RNA was determined against the 100% samples The experiments were performed in triplicate.

From these results (FIG. 4) it was obvious that the addition of betaïne in the isolation improved the elution in the new protocol. The new protocol was as efficient as the standard Boom protocol.

Example 10

To be able to make a statistical evaluation and comparison between new protocol and the standard Boom protocol, 10 samples were analyzed by each protocol. For each example $2 \times 10^5$ molecules in vitro transcribed HIV-1 RNA were spiked in plasma. The Boom protocol was performed with elution in 100 μl H$_2$O. After binding of the RNA to the silica, the new protocol existed of washings with 5M NaSCN, 5M NaCl, 70% ethanol (2×), 15 mM NaCl/10 mM tris, pH 0.5 and elution with 3M betaine in 10 mM tris, pH 8.5. After the isolation a quantitative amplification was performed by adding $10^4$ Qa and $5 \times 10^3$ Qb RNA molecules as internal standards. The results are summarized in table 6 and table 7. By statistical calculations the two methods proof to be identical in performance.

TABLE 6

ECL counts for the RNA's after the NASBA amplification and the average of these signals. The in vitro transcribed HIV-1 RNA is denoted as wt in this table.

| Boom: | $Q_A$ | $Q_B$ | wt | new protocol: | $Q_A$ | $Q_B$ | wt |
|---|---|---|---|---|---|---|---|
| 1 | 797839 | 873594 | 366947 | 1 | 669353 | 971196 | 349116 |
| 2 | 849519 | 883281 | 190842 | 2 | 723736 | 838659 | 302830 |
| 3 | 865491 | 842505 | 264414 | 3 | 756767 | 841488 | 264288 |
| 4 | 738739 | 974851 | 381059 | 4 | 737875 | 906776 | 276051 |
| 5 | 891318 | 963281 | 87410 | 5 | 791250 | 859990 | 247159 |
| 6 | 841075 | 863602 | 279727 | 6 | 755119 | 979499 | 238056 |
| 7 | 780242 | 803434 | 226597 | 7 | 683193 | 890830 | 297602 |
| 8 | 715077 | 890399 | 371066 | 8 | 836213 | 807986 | 96754 |
| | | | | 9 | 739428 | 730010 | 236861 |
| average | 809913 | 886868 | 271008 | average | 743659 | 869604 | 256524 |

TABLE 7

Average the ECL signals of the internal standards and of the wt (HIV-1) RNA. Also is determined the standard deviation (std) of the RNA recovery and the variation coefficient. The ratio of the average ECL signal of the methods is also depicted in this table

| | Boom: | new protocol: | Ratio: |
|---|---|---|---|
| $Q_A$: | 809913 | 743659 | 1,09:1 |
| $Q_B$: | 886868 | 869604 | 1,02:1 |
| wt: | 271008 | 256524 | 1,06:1 |
| % RNA isolated: | 33% | 32% | |
| std | 12,12 | 8,37 | |
| cv | 0,37 | 0,26 | |

Example 11

The same example as described above was performed with in vitro transcribed HCV RNA spiked in whole blood. For each sample $5.9 \times 10^5$ molecules HCV RNA were spiked in whole blood. The standard Boom protocol was performed with elution in 100 μl H$_2$O. After binding of the RNA to the silica, the new protocol existed of washings with 5M NaSCN, 5M NaCl, 70% ethanol (2×), 15 mM NaCl/10 mM tris, pH 6.5 and elution with 3M betaïne in 10 mM tris, pH 8.5. After the isolation a quantitative amplification was performed by adding $10^4$ Qe and $5 \times 10^3$ Qf RNA molecules as internal standards.

The results are shown in tables 8 and 9. Statistical calculations revealed that both methods proof to be identical

TABLE 8

ECL counts for the RNA's after the NASBA amplification and the average of these signals. The in vitro transcribed HCV RNA is denoted as wt in this table.

| Boom: | $Q_E$ | $Q_F$ | wt | new protocol: | $Q_E$ | $Q_F$ | wt |
|---|---|---|---|---|---|---|---|
| 1 | 27486 | 19826 | 25112 | 1 | 102509 | 52062 | 27491 |
| 2 | 31549 | 19906 | 29220 | 2 | 189642 | 70934 | 79123 |
| 3 | 32152 | 24979 | 34910 | 3 | 114150 | 50641 | 39092 |
| 4 | 32416 | 26361 | 35251 | 4 | 89838 | 108772 | 63296 |
| 5 | 39094 | 31323 | 38752 | 5 | 128956 | 60813 | 52171 |
| 6 | 42471 | 31955 | 40001 | 6 | 114181 | 43156 | 92707 |
| 7 | 47300 | 33755 | 42681 | 7 | 183674 | 61813 | 71924 |
| 8 | 48125 | 46406 | 52939 | 8 | 18322 | 57185 | 38332 |
| 9 | 50074 | 47738 | 64116 | 9 | 176058 | 82952 | 18480 |
| 10 | 52082 | 47813 | | 10 | 212759 | 24901 | |
| 11 | 54879 | 51822 | | 11 | 183631 | 56489 | |
| average | 41603 | 34717 | 40331 | average | 137611 | 60883 | 53624 |

TABLE 9

Average the ECL signals of the internal standards and of the wt (HCV) RNA. Also is determined the standard deviation (std) of the RNA recovery and the variation coefficient. The ratio of the average ECL signal of the methods is also depicted in this table.

| | Boom: | new protocol: | Ratio: |
|---|---|---|---|
| $Q_E$: | 41603 | 137611 | 1:3,31 |
| $Q_F$: | 34717 | 60883 | 1:1,75 |
| wt: | 40331 | 53624 | 1:1,33 |
| % RNA isolated: | 8% | 5,67% | |
| std | 2,49 | 3,30 | |
| cv | 0,31 | 0,58 | |

What is claimed is:

1. In a method for the isolation of nucleic acid from nucleic acid containing starting material in which the starting material is contacted with a chaotropic substance and, either simultaneously or subsequently, with a nucleic acid binding solid phase, whereafter the nucleic acid binding solid phase is subject to a washing procedure and, optionally, the nucleic acid is eluted from the nucleic acid binding solid phase, wherein the improvement is in that the washing procedure comprises the steps of washing the solid phase with
   one or more high salt buffer solution(s), followed by
   a low salt buffer solution.

2. The method according to claim 1, wherein the pH of the high salt buffer solution(s) lies approximately between 6 and 8.

3. The method according to claim 2, wherein a high salt buffer is used comprising 1–10M NaSCN/10 mM tris.

4. The method according to claim 3, wherein the high salt buffer comprises 5M NaSCN/10 mM tris and has a pH of 6.5.

5. The method according to claim 2, wherein a high salt buffer is used comprises 1–10 M NaCl/10 mM tris.

6. The method according to claim 5, wherein the high salt buffer comprises 5M NaCl/10 mM tris and has a pH of 6.5.

7. The method according to claim 1, wherein more than one different high salt buffer solutions are used.

8. The method according to claim 7, wherein a first high salt buffer is used comprising 1–10 M NaSCN/10 mM tris and a second high salt buffer is used comprising 1–10 M NaCl10 mM tris, both buffers having a pH approximately between 6 and 8.

9. The method according to claim 8, wherein the washing procedure comprises the steps of,
   washing with a first high salt buffer comprising 1–10M NaSCN/10 mM tris, with a pH approximately between 6 and 8; and
   washing with a second high salt buffer comprising 1–10M NaCl/10 mM tris, with a pH approximately between 6 and 8.

10. The method according to claim 1, wherein the high salt washing step is followed by washing with a alcoholic solution comprising a lower alkyl alcohol.

11. The method according to claim 10, wherein the alcoholic solution comprises 60–70% ethanol.

12. The method according to claim 11, wherein the alcoholic solution comprises 63% ethanol.

13. The method according to claim 10, wherein the alcoholic solution comprises isopropanol.

14. The method according to claim 1, wherein the low salt buffer used comprises 2–20 mM NaCl/10 mM tris.

15. The method according to claim 1, wherein a low salt buffer is used with a pH approximately between 6–8.

16. The method according to claim 14, wherein the low salt buffer comprises 15 mM NaCl/10 mM tris pH=6.5.

17. The method according to claim 14, wherein the washing procedure comprises two subsequent washes with the low salt buffer.

18. The method according to claim 1, wherein the washing procedure comprises the steps of:
   washing with a first high salt buffer comprising 5M NaSCN/10 mM tris pH=6.5
   washing with a second high salt buffer comprising 5M NaCl/10 mM tris pH=6.5 washing with 70% ethanol and, washing with a low salt buffer comprising 15 mM NaCl/ 10 mM tris ph=6.5.

19. The method according to claim 1, wherein after the last washing step the nucleic acid is eluted from the solid phase by treating the solid phase with a buffer containing 10 mM tris pH=8.5 and a chaotropic agent.

20. The method according to claim 19, wherein the chaotropic agent is betaine.

21. The method according to claim 20, wherein betaine is used in a concentration of 3M.

* * * * *

UNITED STATES PATENT AND TRADEMARK OFFICE
CERTIFICATE OF CORRECTION

PATENT NO.   : 6,465,639 B1
DATED        : October 15, 2002
INVENTOR(S)  : van Gemen et al.

It is certified that error appears in the above-identified patent and that said Letters Patent is hereby corrected as shown below:

Column 11,
Lines 5-7, "Statistical calculations revealed that both methods proof to be identical" should read -- Statistical calculations revealed that both methods proof to be identical in performance --

Column 12,
Line 28, "NaCl10" should read -- NaCl/10 --

Signed and Sealed this

Third Day of June, 2003

JAMES E. ROGAN
*Director of the United States Patent and Trademark Office*